United States Patent [19]

Wheatman

[11] Patent Number: 5,733,263
[45] Date of Patent: Mar. 31, 1998

[54] THERMAL RETENTION SYSTEM AND METHOD

[75] Inventor: Steven Wheatman, Lower Gwynedd, Pa.

[73] Assignee: Cabot Technology Corporation, Wilmington, Del.

[21] Appl. No.: 680,108

[22] Filed: Jul. 15, 1996

Related U.S. Application Data

[63] Continuation of Ser. No. 309,048, Sep. 20, 1994, abandoned.

[51] Int. Cl.$^6$ ........................................... A61M 37/00
[52] U.S. Cl. ........................................... 604/141; 604/131
[58] Field of Search ........................ 604/113, 114, 604/131, 141, 146, 153, 408, 259; 607/96

[56] References Cited

U.S. PATENT DOCUMENTS

| | | | |
|---|---|---|---|
| 1,113,757 | 10/1914 | Crutcher et al. | 604/113 |
| 3,247,851 | 4/1966 | Seibert . | |
| 3,590,215 | 6/1971 | Anderson et al. | 604/114 |
| 3,895,741 | 7/1975 | Nugent . | |
| 4,039,775 | 8/1977 | Andra . | |
| 4,149,066 | 4/1979 | Niibe . | |
| 4,163,896 | 8/1979 | McAvinn et al. . | |
| 4,167,663 | 9/1979 | Granzow, Jr. et al. . | |
| 4,272,673 | 6/1981 | Semanaz et al. . | |
| 4,314,143 | 2/1982 | Bilstad et al. . | |
| 4,430,078 | 2/1984 | Sprague . | |
| 4,453,669 | 6/1984 | Karla et al. . | |
| 4,455,481 | 6/1984 | Van Hoof et al. . | |
| 4,539,005 | 9/1985 | Greenblatt . | |
| 4,612,710 | 9/1986 | Fernwood et al. . | |
| 4,709,135 | 11/1987 | Dietrich et al. . | |
| 4,751,495 | 6/1988 | Whitman . | |
| 4,844,074 | 7/1989 | Kurucz . | |
| 4,906,816 | 3/1990 | van Leerdam | 604/114 |
| 4,908,497 | 3/1990 | Hjortsberg . | |
| 5,013,303 | 5/1991 | Tamari et al. . | |
| 5,057,667 | 10/1991 | Bell et al. . | |
| 5,061,241 | 10/1991 | Stephens, Jr. et al. | 604/114 |
| 5,125,900 | 6/1992 | Teves . | |
| 5,129,033 | 7/1992 | Ferrara et al. . | |
| 5,183,994 | 2/1993 | Bowles et al. . | |
| 5,199,604 | 4/1993 | Palmer et al. . | |
| 5,207,645 | 5/1993 | Ross et al. . | |
| 5,211,626 | 5/1993 | Frank et al. | 604/65 |
| 5,252,303 | 10/1993 | Goof . | |
| 5,368,569 | 11/1994 | Sanese | 604/113 |
| 5,419,772 | 5/1995 | Teitz et al. | 604/146 |

OTHER PUBLICATIONS

Cabot Medical Corporation, Laparoscopic Irrigation & Instrumentation Systems, 1993.
Douglas E. Ott, M.D., Laparoscopic Hypothermia, Journal of Laparoendoscopic Surgery, vol. 1, No. 3, 1991.
Michael R. Seitzinger, M.D. & Lenore S. Dudgeon, C.R.N.A., Decreasing the Degree of Hypothermia During Prolonged Laparoscopic Procedures, The Journal of Reproductive Medicine, vol. 38, No. 7, Jul. 1993.
Cabot Technology Corporation, NIAGARA™ 3.0 Liter High Flow Irrigator Produce Manual, 1993.

*Primary Examiner*—Jennifer Bahr
*Assistant Examiner*—Eric F. Winakur
*Attorney, Agent, or Firm*—Austin R. Miller

[57] ABSTRACT

An apparatus is provided for heating fluid contained in one or more bags and delivering the fluid from at least one bag to a surgical patient. The apparatus includes a housing sized and shaped to enclose at least one bag containing fluid and having a door positioned to provide access to an interior of the housing. The apparatus also includes an inflatable bladder mounted in the interior of the housing and connected to a source of pressurized fluid for inflation. The inflatable bladder is positioned within the housing for exerting force against at least one bag mounted within the housing. The apparatus also includes a heater mounted adjacent the housing door in heat transfer relationship with the fluid in at least one bag. The invention also provides a method for maintaining the temperature of fluid contained in one or more bags and for delivering the fluid from at least one bag to a surgical patient.

29 Claims, 13 Drawing Sheets

THERMAL RETENTION SYSTEM AND METHOD

This application is a continuation of application Ser. No. 08/309,048, filed Sep. 20, 1994, now abandoned.

BACKGROUND OF THE INVENTION

This invention relates to a system for delivering irrigation fluid to a surgical patient and for maintaining the fluid at a desired temperature throughout a surgical procedure. It also relates to a method for delivering irrigation fluid at a uniform elevated temperature.

FIELD OF THE INVENTION

There has been a recent and dramatic surge in the use of advanced laparoscopic procedures. Such procedures sometimes require increased operating and anesthesia time. Recent studies have shown that prolonged laparoscopic procedures may pose some risk of hypothermia to the surgical patient. For discussions of this phenomenon, see Douglas E. Ott, M.D., "Laparoscopic Hypothermia," *Journal of Laparoendoscopic Surgery*, p. 127, Vol. 1, No. 3, 1991; and Michael R. Seitzinger, M.D., "Decreasing the Degree of Hypothermia During Prolonged Laparoscopic Procedures," *The Journal of Reproductive Medicine*, p. 511, Vol. 38, No. 7, July 1993.

Surgeons have attempted to reduce the risk of hypothermia by using heated pads (sometimes referred to as "K-pads") beneath the patient, patient warmers (such as the BAIR HUGGER product) and warm intravenous solution. These methods have been attempted alone and in combination.

The human body temperature on average is about 37° C. and operating room temperatures are much cooler, averaging about 21° C. Accordingly, room-temperature fluids are well below body temperature and pre-warmed fluids cool rapidly.

Attempts have been made to heat and maintain fluids, such as irrigation fluids, at a temperature approximating normal body temperature during surgical operations or other medical procedures. In U.S. Pat. No. 5,129,033, Ferrara et al disclosed an irrigation and lavage liquid warming bowl for use during medical-surgical procedures. The Ferrara warming bowl had a submerged heater device for maintaining pre-heated fluid at body temperature. However, the Ferrara system was open and unprotected against fluid contamination.

In U.S. Pat. No. 5,199,604, Palmer et al disclosed a system for delivering a variety of liquids to a treatment site. The complicated Palmer system provided a heater near a delivery handpiece for heating irrigation fluid as it was pumped from the system and into the patient.

In U.S. Pat. No. 3,247,851, Seibert disclosed a gravity flow apparatus for keeping a pad or compress moist. The Seibert apparatus included a suspended receptacle surrounded by a rubber jacket within which electric resistance heating wires were embedded. However, the Seibert apparatus provided no pump for varying liquid pressure.

Accordingly, there is a great and thus far unsatisfied demand for an irrigation fluid pump which maintains irrigation fluid at body temperature throughout a surgical procedure.

OBJECTS OF THE INVENTION

It is an object of this invention to provide an irrigation pump which overcomes the problems associated with prior art designs.

It is another object of the invention to provide an irrigation pump having a mechanism for efficient control of irrigation fluid pressure and flow.

It is a further object of the invention to provide an irrigation pump having a housing for containing one or more bags of irrigation fluid.

It is yet another object of this invention to provide an irrigation pump housing having means for heating and maintaining irrigation fluid at body temperature throughout an operative procedure.

It is still another object of this invention to provide an irrigation pump housing which senses the temperature of irrigation fluid contained in one or more bags within the housing.

Other objects of the invention will be apparent to one of ordinary skill in this art in view of the detailed disclosure herein.

SUMMARY OF THE INVENTION

This invention provides a system for pumping irrigation fluid from one or more bags to a surgical patient and for heating and maintaining the temperature of the irrigation fluid near body temperature throughout the surgical procedure. The system has a pump housing as well as fluid delivery tubes for transport of irrigation fluid. The pump is a diaphragm-type pump positioned to exert force against one or more irrigation fluid bags to cause pressurized flow of the irrigation fluid through the delivery tubing to the patient. The pump housing has a heat source in its door to heat and maintain irrigation fluid at or near body temperature throughout the surgical procedure. The housing door also has a temperature sensor so that the irrigation fluid temperature can be monitored and controlled throughout the surgical procedure.

This invention also provides a method for delivering irrigation fluid at a temperature approximating the body temperature of a surgical patient. The method includes placing irrigation fluid bags in a pump housing. A heat source and a temperature sensor are provided on the pump housing door to heat and maintain and measure the temperature of the irrigation fluid throughout the surgical procedure. The pump is actuated to exert force against the irrigation fluid in one or more bags, thereby delivering irrigation fluid from the bags in the pump housing, through delivery tubes and into the surgical patient.

DETAILED DESCRIPTION OF THE INVENTION

Figure 1:
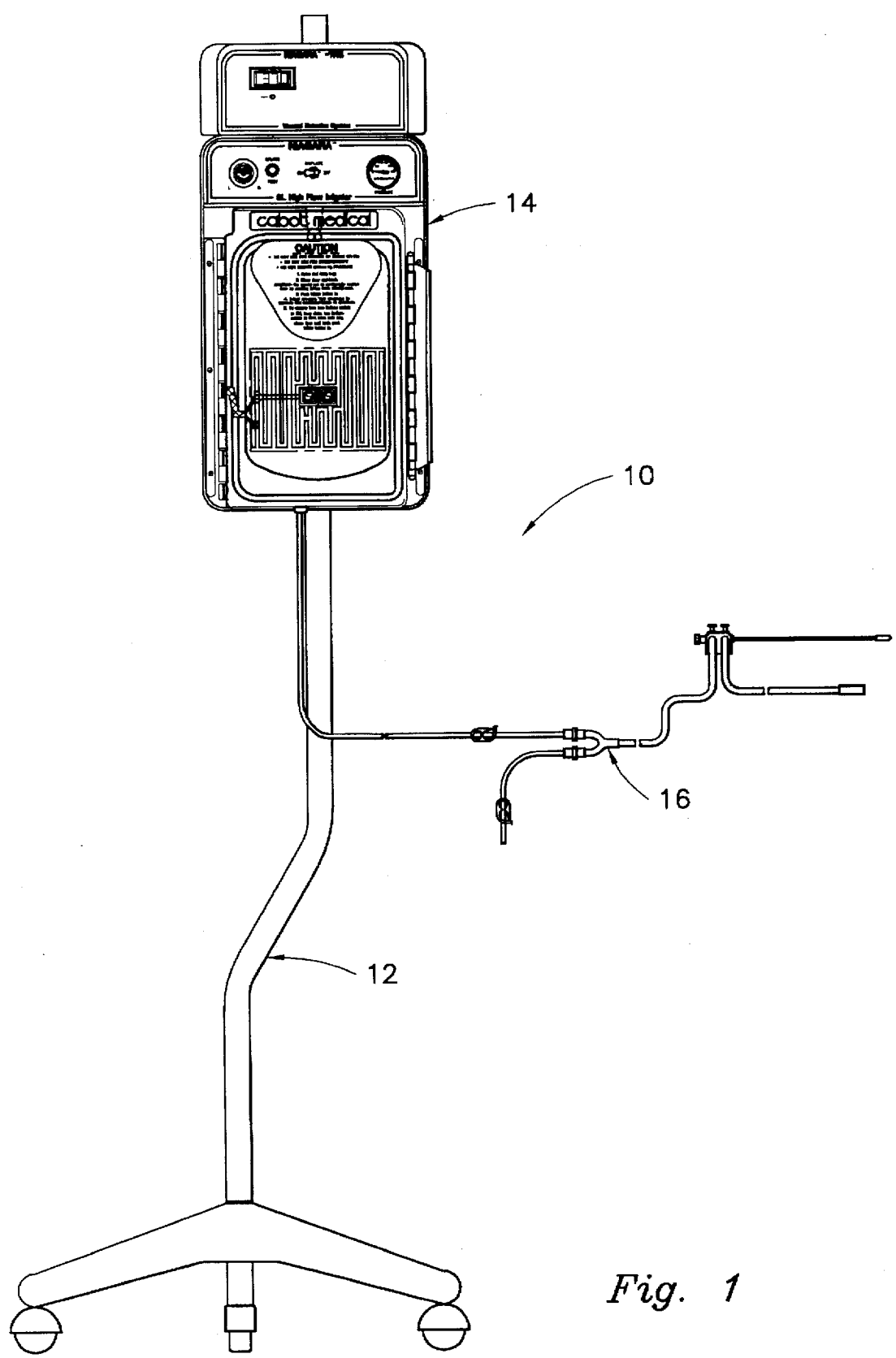
FIG. 1 shows one form of thermal retention system embodying features of this invention.

The following description is intended to refer to the specific embodiments of the invention illustrated in the drawings. This description is not intended to define or limit the scope of the invention, which is defined separately in the claims that follow. Referring to FIG. 1, the numeral "10" designates a thermal retention system mounted to a wheeled stand 12. Thermal retention system 10 has a fluid pump 14 for delivering fluid (not shown), such as irrigation fluid, through a fluid delivery assembly 16. Thermal retention system 10 is adapted for use with irrigation fluids such as saline solution, ringers lactate, glycine, SORBITOL solution or sterile water. System 10 can, however, be used to heat and maintain the temperature of any fluid.

Figure 2:
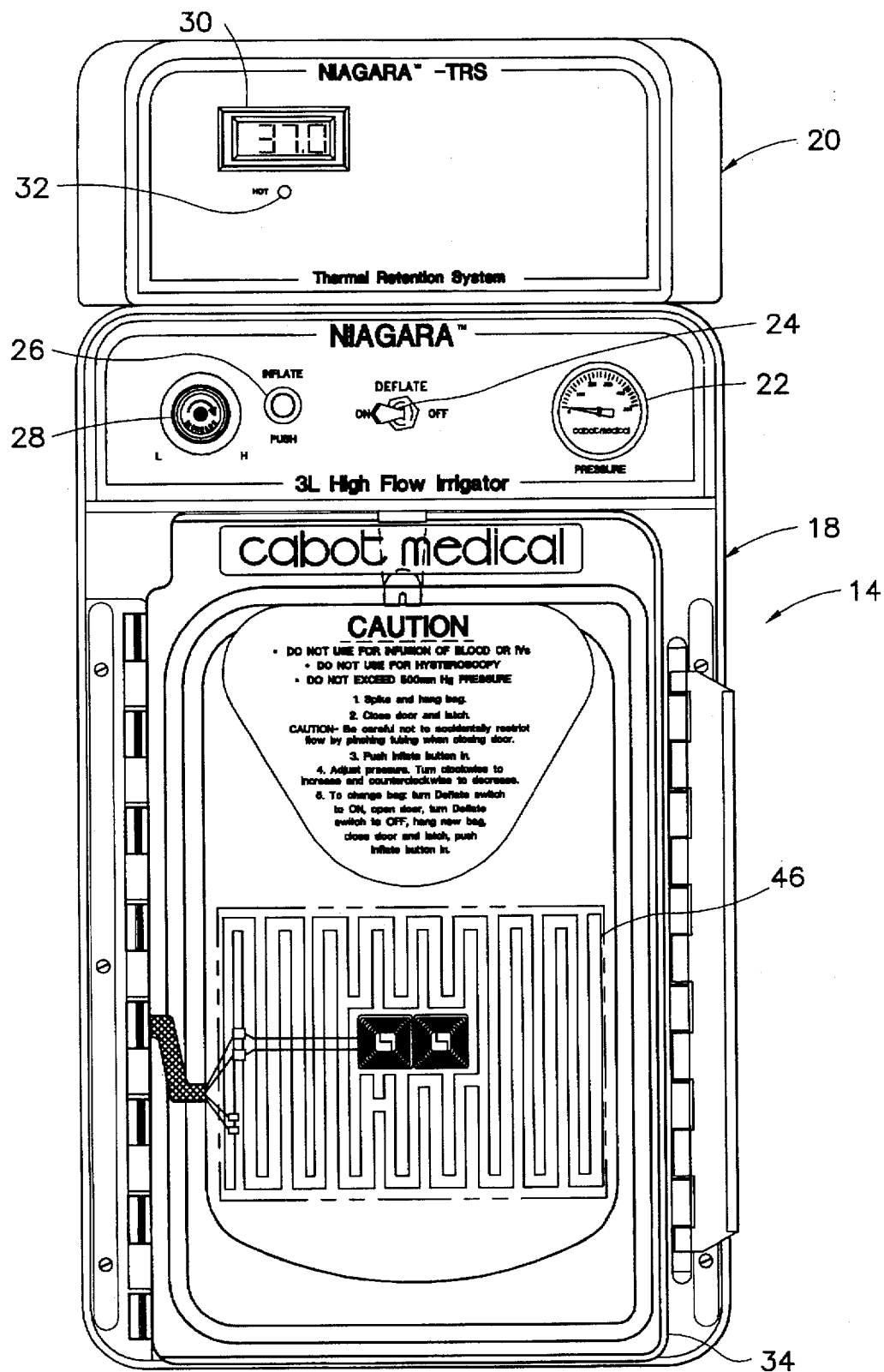
FIG. 2 is a front view of a fluid pump adapted for use in a thermal retention system embodying features of this invention.

FIG. 2 shows details of the front face of fluid pump 14 of thermal retention system 10. Pump 14 has a pump housing 18 on top of which is mounted a heater control unit 20. The bodies of pump housing 18 and heater control unit 20 are preferably formed from ABS, but are optionally formed from any appropriate metal or plastic.

Pump housing 18 has a pressure gauge 22 which indicates the amount of regulated pressure. Pump housing 18 also has a toggle switch 24 to deactivate pump 14 and release pressure from the irrigation fluid. Pump housing 18 also has a button 26 to activate pump 14 to pressurize the irrigation fluid. A regulator knob 28 is provided to regulate the pressure applied to the irrigation fluid supply when pump 14 is activated.

Pump housing 18 also has a door 34 with an integral heating element assembly 46. Heating element assembly 46 has a heating element and temperature sensor, both of which will be described below with reference to FIGS. 3 and 8.

Heater control unit 20 has a digital temperature display 30 for displaying the temperature of the irrigation fluid. The temperature is displayed in degrees centigrade (as shown) or in degrees fahrenheit. Temperature display 30 is optionally an analog gauge or any other known indicator. Heater control unit 20 also has a visual alarm condition indicator 32 located below digital temperature display 30 to provide a visual indication when fluid temperature exceeds a pre-determined maximum. Alarm condition indicator 32 is preferably an LED but may be any other known visual or audible alarm.

Figure 3:
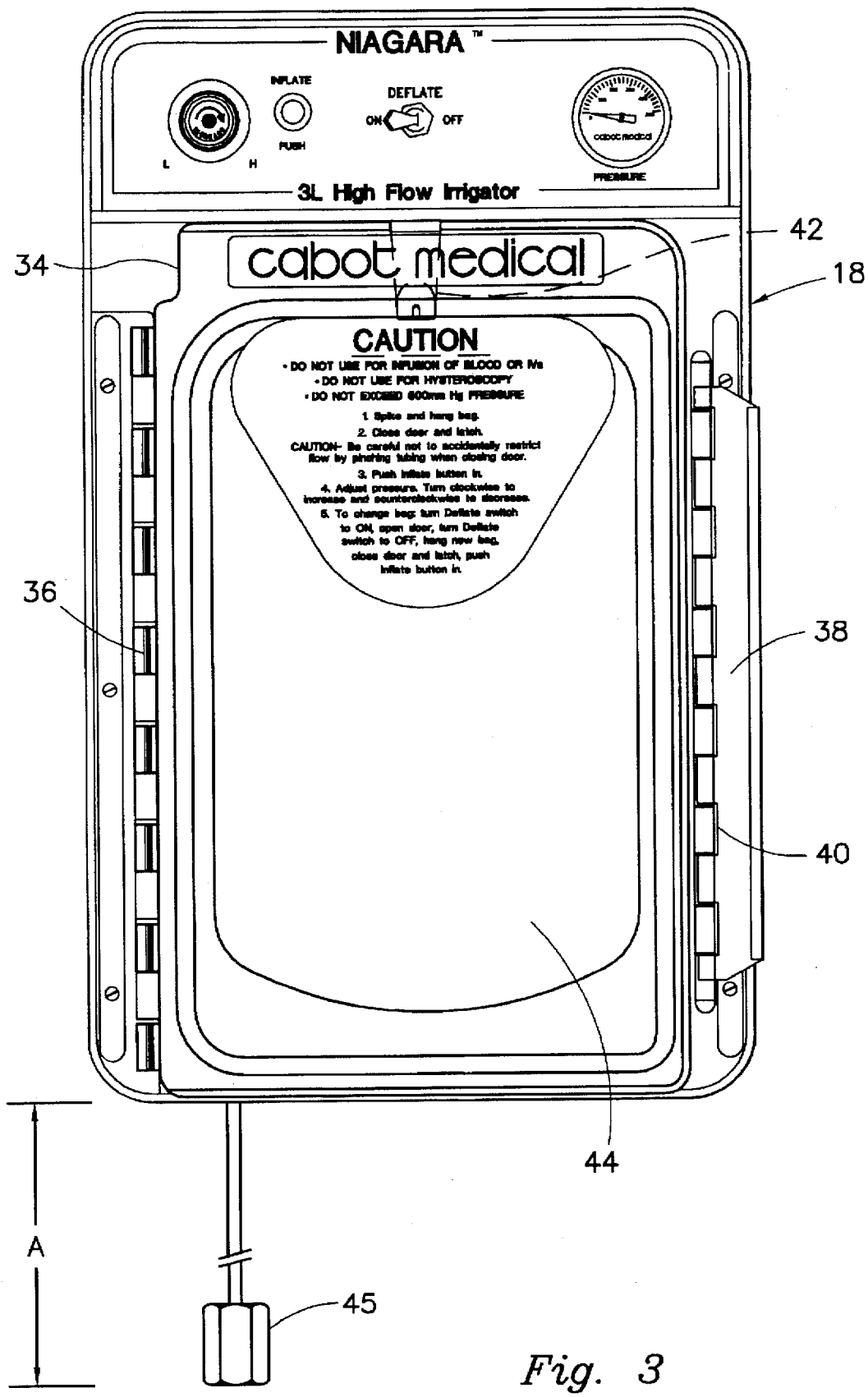
FIG. 3 is a front view of an embodiment of a pump housing component of the fluid pump shown in FIG. 2.

Referring now to FIG. 3, pump door 34 is mounted to pump housing 18 by means of a hinge 36 located at the left side of pump housing 18. A clasp 38 is attached by means of a hinge 40 at the right side of pump housing 18 so that clasp 38 can be pivoted from the open position shown in FIG. 3 to a closed position, thereby capturing pump door 34 and preventing door 34 from opening. A hook 42 (shown in phantom lines) is mounted at the top of pump door 34 so that it extends into pump housing 18. Hook 42 is provided to support a bag of irrigation fluid (not shown) within pump housing 18 as will be described in detail below. Additional hooks similar or identical to hook 42 may be provided to hold additional bags of irrigation fluid.

Pump door 34 is provided with a window 44 on which heating element assembly 46 (not shown) is mounted. Window 44 is preferably clear so that the amount of fluid remaining can be monitored. A pressurized gas supply line 45 is provided for connecting pump housing 18 to a gas supply (not shown). The gas supply is optionally a gas cylinder or a continuous gas supply of the type often found in hospital operating rooms. Pressurized gas supply line 45 extends from pump housing 18 a distance A sufficient to allow mobility of thermal retention system 10.

Figure 4:
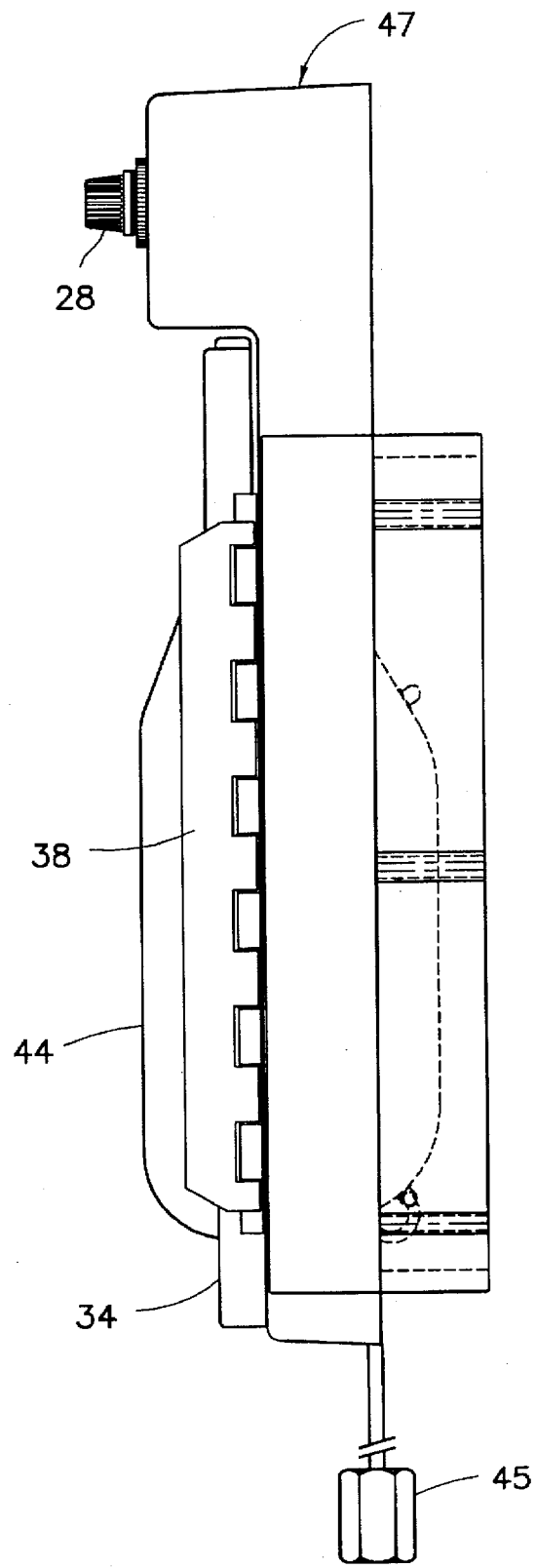
FIG. 4 is a side view of an embodiment of a front cover assembly component of the pump housing component shown in FIG. 3.

FIG. 4 shows a side view of a front cover assembly portion 47 of pump housing 18. This view also shows regulator knob 28, clamp 38, gas supply line 45 and window 44 on pump door 34. Note that window 44 on pump door 34 preferably extends outward from pump door 34.

Figure 5:
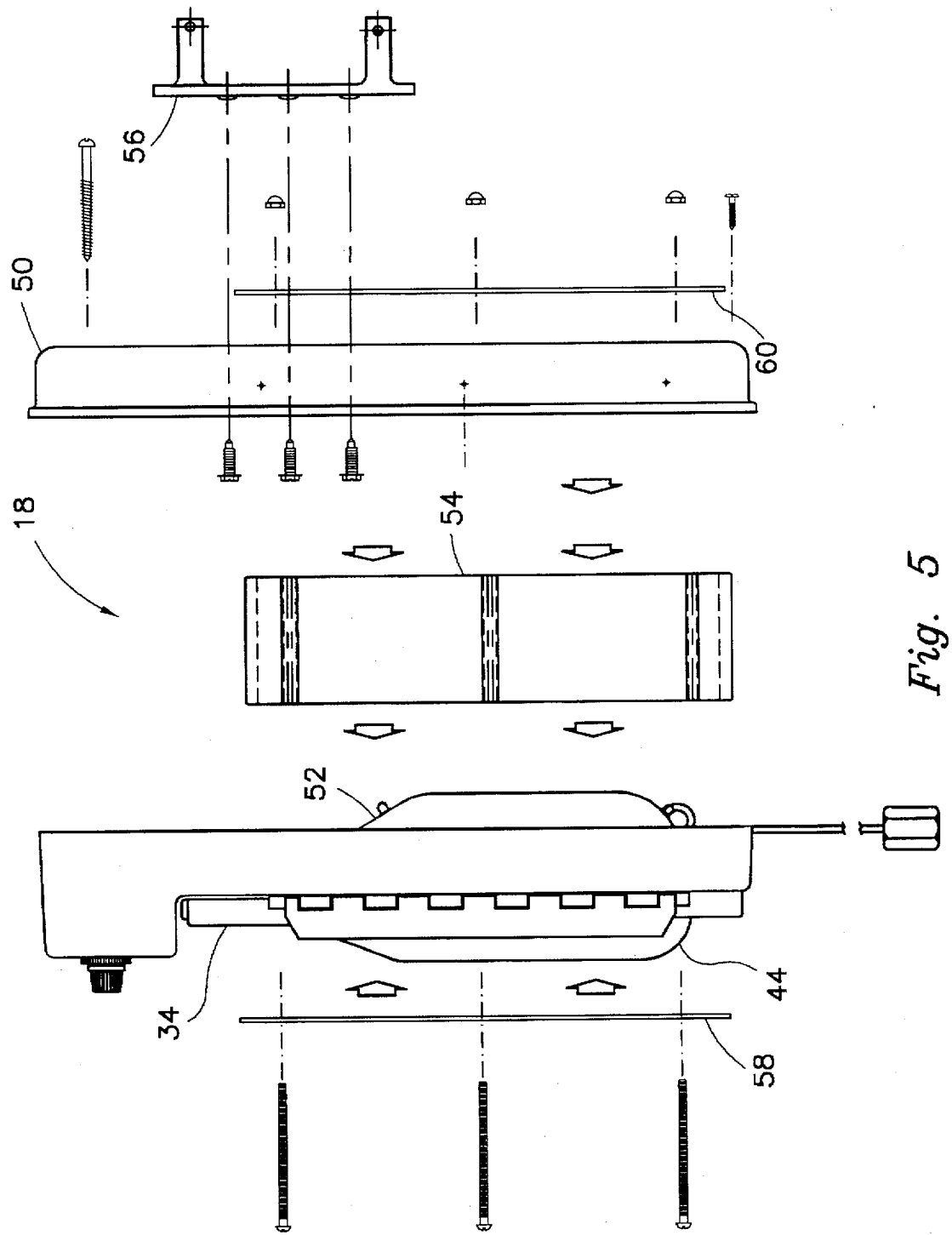
FIG. 5 is an exploded side view of the front cover assembly shown in FIG. 4.

FIG. 5 provides an exploded view of pump housing 18. Pump housing 18 has a front cover sub-assembly and a back cover 50. The front cover sub-assembly contains, in addition to pump door 34 and window 44, a bladder 52. Bladder 52 is inflatable and deflatable for pressurizing and depressurizing irrigation fluid in one or more bags within pump housing 18. The exact configuration and operation of bladder 52 will be described in detail below.

Pump housing 18 also includes a bracket 54 which is mounted to surround and protect bladder 52. A mounting bracket 56 is attached to pump housing 18 to provide a means for connecting pump housing 18 and pump 14 to a stand such as wheeled stand 12 shown in FIG. 1. Pairs of support straps 58 and 60 are provided to support various hardware fastened to assemble pump housing 18 as shown in FIG. 5.

Figure 6:
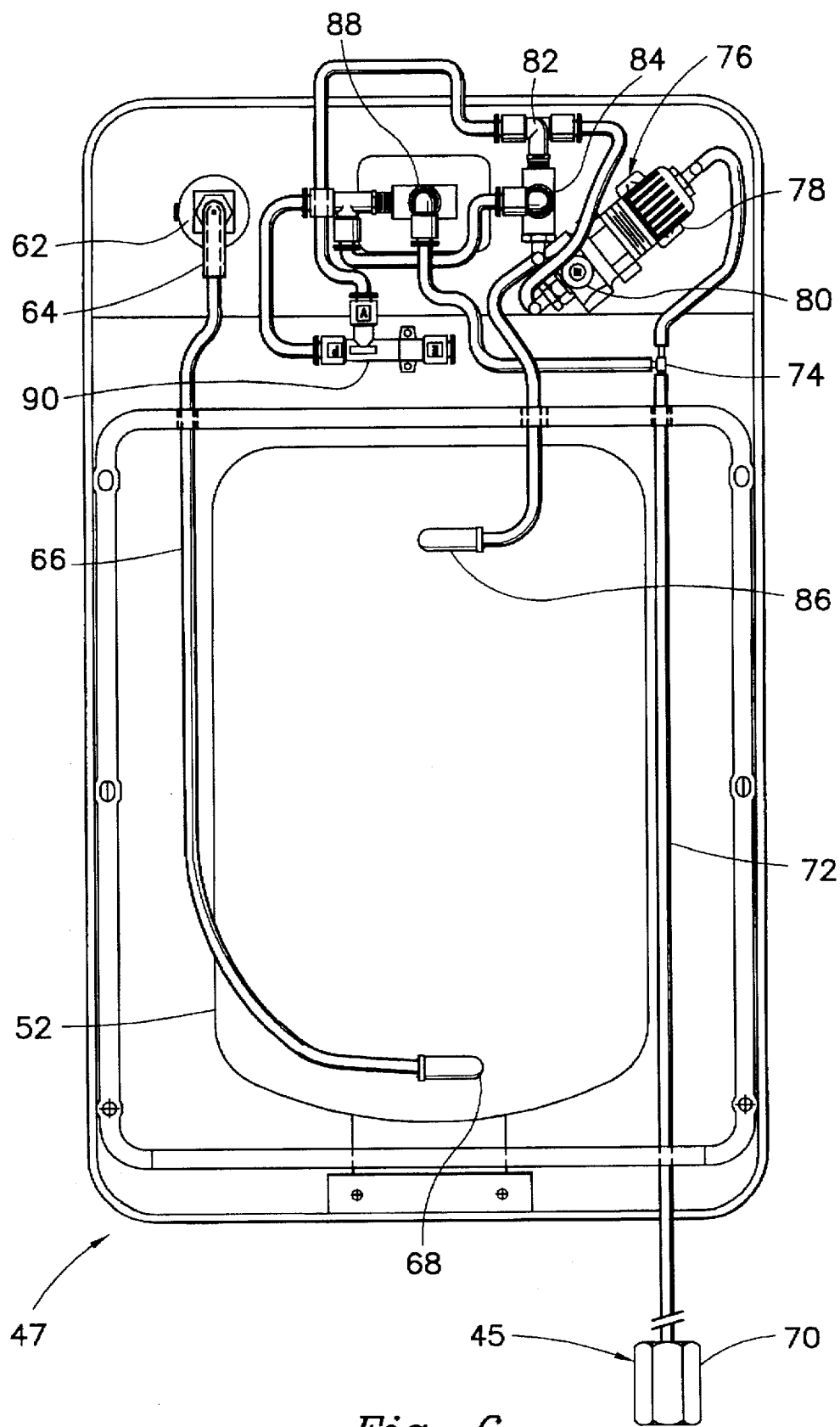
FIG. 6 is a rear view of the front cover assembly shown in FIGS. 4 and 5.

A rear view of front cover assembly 47 of pump housing 18 is illustrated in FIG. 6. Front cover assembly 47 has a pressure gauge assembly 62 connected to pressure gauge 22 shown in FIG. 2. Pressure gauge assembly 62 is connected by means of a fitting 64 to a length of tubing 66. Tubing 66 is connected to bladder 52 toward the bladder's bottom. The connection between tubing 66 and bladder 52 is made using a solvent 68 such as cyclohexanone solvent.

A fitting 70 is provided on gas supply line 45 for connection to a pressure source (not shown) to allow flow of pressurized gas into a tubing length 72. Tubing 72 is divided at a barbed tee 74 forming two paths. The first path leads to an actuator 84 connected to button 26 (FIG. 2). Between barbed tee 74 and actuator 84 is a relief valve assembly 76 including a pressure regulator 78 and a pressure relief valve 80. Regulator 78 is connected to regulator knob 28 (FIG. 2) to permit manual gas pressure regulation by turning regulator knob 28 to control the pressure preferably between zero (0) and ten (10) PSI. Pressure relief valve 80 is connected in series with regulator 78 and is calibrated to relieve gas pressure if the pressure exceeds a pre-determined maximum. Pressurized gas flows from relief valve assembly 76 to actuator 84 after passing through a tee 82.

The second path from barbed tee 74 leads to an actuator 88 connected to toggle switch 24 (FIG. 2). Both actuators 84 and 88 are connected via tubing to a vacuum ejector 90. Actuator 84 is also connected via tubing to a fitting 86 attached to a top portion of bladder 52.

The assembly shown in FIG. 6 permits the introduction of pressurized gas into pump housing 18 and permits the regulation of the pressure, relief of excess pressure, delivery of regulated pressure to bladder 52 for inflation, evacuation of pressurized gas to deflate bladder 52, and continuous measurement of gas pressure within bladder 52. The operation of pump 14 of thermal retention system 10 will be described in further detail below.

Figure 7:
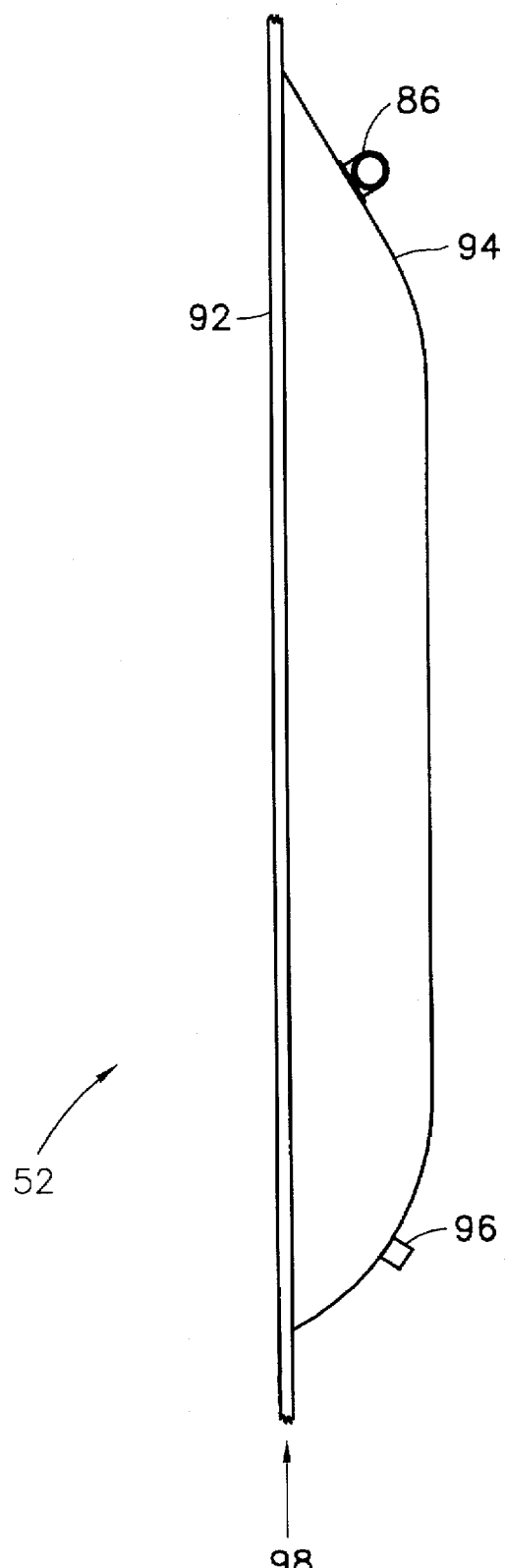
FIG. 7 is a side view of one form of bladder adapted for use in the pump housing component shown in FIG. 3.

Referring to FIG. 7, details of bladder 52 in a deflated condition are shown. Bladder 52 has a flat surface 92 and a contoured surface 94. An outlet 96 is provided near the bottom end portion of contoured surface 94 to which tubing 66 (FIG. 6) is connected. Fitting 86 is provided near the top of contoured surface 94. Contoured surface 94 is hermetically sealed to flat surface 92 by means of a weld 98 such as a radio-frequence (RF) weld.

Details of heating element assembly 46 introduced in FIG. 2 are described with reference to FIG. 8. Heating element assembly 46 has a heating element 100 formed on a substrate 102. Heating element 100 is a continuous electrical conductor such as a wire. Heating element 100 is preferably a resistive wire having a diameter of at least about 0.0008 inch to about 0.010 inch or larger. Heating element 100 is preferably formed from copper, nickel, nickel-alloy, chromium, aluminum or iron but is optionally formed from any other conductive material with resistance characteristics wherein power supply to the material causes heat generation. Heating element 100 most preferably has a heating resistance of about 28 ohms for a system containing one large bag of irrigation fluid having a volume of about three liters. A system containing multiple smaller irrigation fluid bags would require a greater heating resistance. For example, a two-liter system containing two one-liter bags preferably includes two heating elements each having a heating resistance of about 56 ohms. Any suitable resistance is contemplated. Heating element 100 is optionally a continuous ribbon or conductive coating.

Surrounded by heating element 100 is heat sensor 104. Heat sensor 104 is preferably an RTD-type sensor formed from resistive wires wherein wire resistance varies proportionally with temperature. Heat sensor 104 is optionally a thermistor-type sensor or a thermocouple. Heat sensor 104 is preferably formed from platinum, nickel, copper or nickel alloy, although any other suitable material can be used. Heat sensor 104 most preferably has a resistance of about 100 ohms although any resistance suitable for temperature measurement is contemplated.

Electrical connection is made to heating element 100 with conductors 106 and to heat sensor 104 with conductors 108. Conductors 106 and 108 are, in turn, provided with a length L and are connected to heater control unit 20 (FIG. 2) for control of heating element 100 and display of the temperature sensed by heat sensor 104.

Substrate 102 is preferably flexible mylar or polyester but may also be an acrylic, acetate or any other suitable material. Substrate 102 has a width W and height H suitable for mounting on window 44 on door 34 of pump housing 18. Substrate 102 is preferably clear so as to not compromise visibility through window 44. Accordingly, substrate 102 is most preferably formed from optical grade, flexible material having good transparency. An 82% minimum transparency has been found to be ideal but other degrees of transparency are acceptable. Substrate 102 is preferably provided with an adhesive backing to facilitate mounting of substrate 102 on window 44. Optionally, heating element 100 and heat sensor 104 are formed directly into or on the surface of window 44.

Figure 9:
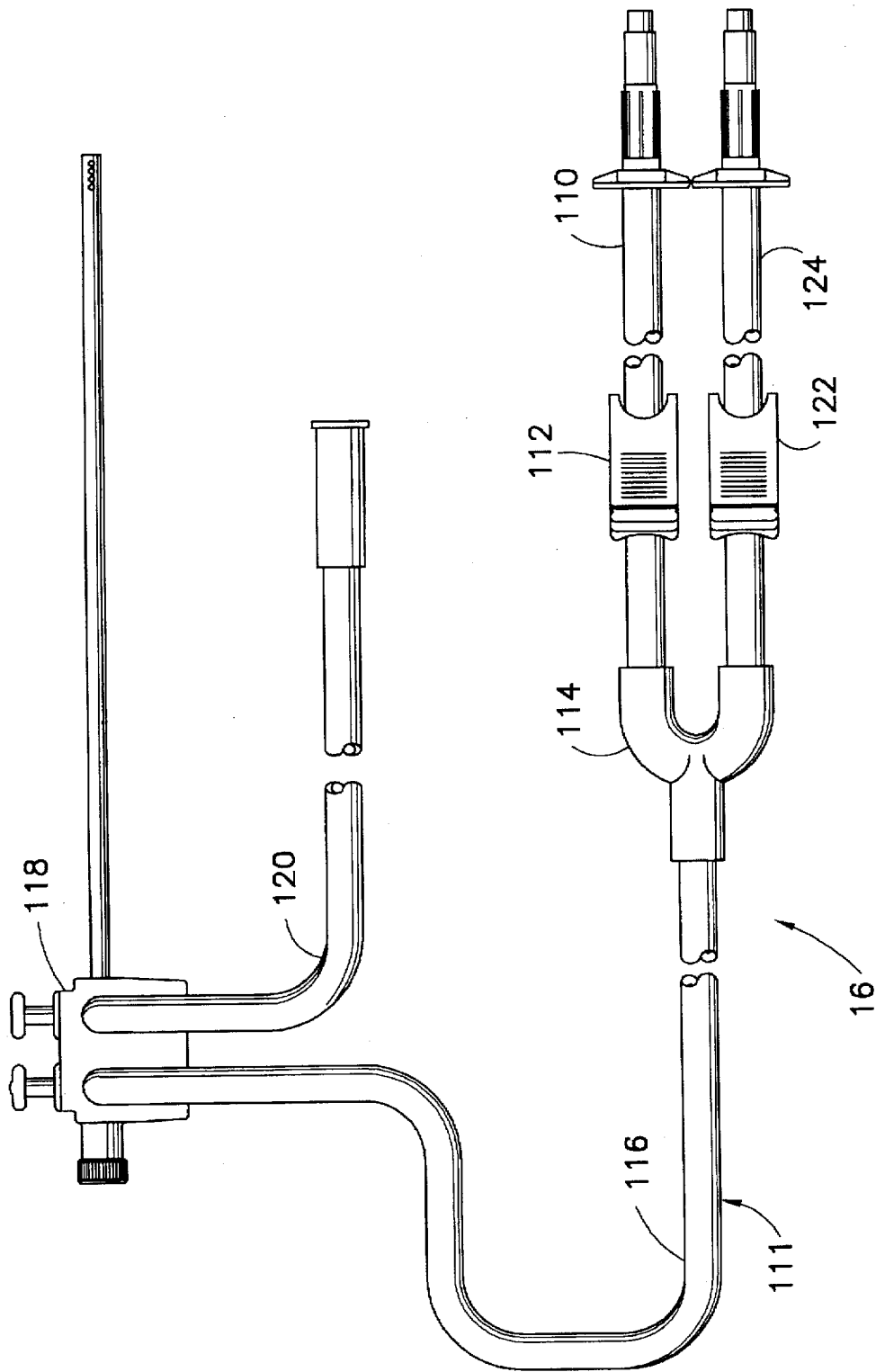
FIG. 9 shows one of fluid delivery assembly adapted for use in a thermal retention system embodying features of this invention.

FIG. 9 provides a schematic view of fluid delivery assembly 16 first introduced with reference to FIG. 1. The embodiment of fluid delivery assembly 16 shown in FIG. 9 includes a suction and irrigation instrument 118 adapted for introduction into the surgical patient. A suitable probe 118 is the CORSON Disposable Suction/Irrigation Probe or NEZHAT Reusable Suction/Irrigation Probe available from Cabot Medical Corporation, 2021 Cabot Boulevard West, Langhorne, Pa. 19047. Suction and irrigation instrument 118 allows aspiration of fluid, smoke and tissue and also permits irrigation to clear debris and improve visualization.

Connected to suction and irrigation instrument 118 is a length of tubing 120 through which fluid is evacuated from thermal retention system 10. Also attached to instrument 118 is a tubing assembly 111 having a tubing length 116 connected to instrument 118 and terminating in a "Y" 114. Connected to "Y" 114 are tubing lengths 110 and 124, both of which terminate in a fitting. Tubing length 110 is provided with a finger actuable stop 112 and tubing length 124 is provided with a similar stop 122. Tubing length 110 is connected to one or more bags of irrigation fluid mounted within pump 14 of thermal retention system 10. Accordingly, irrigation fluid is pumped from pump 14, through tubing length 110, past "Y" 114, through tubing length 116 and into a surgical patient through instrument 118. Tubing length 124 is connected, for example, to an insufflation unit or other source of pressurized gas.

Figure 10:
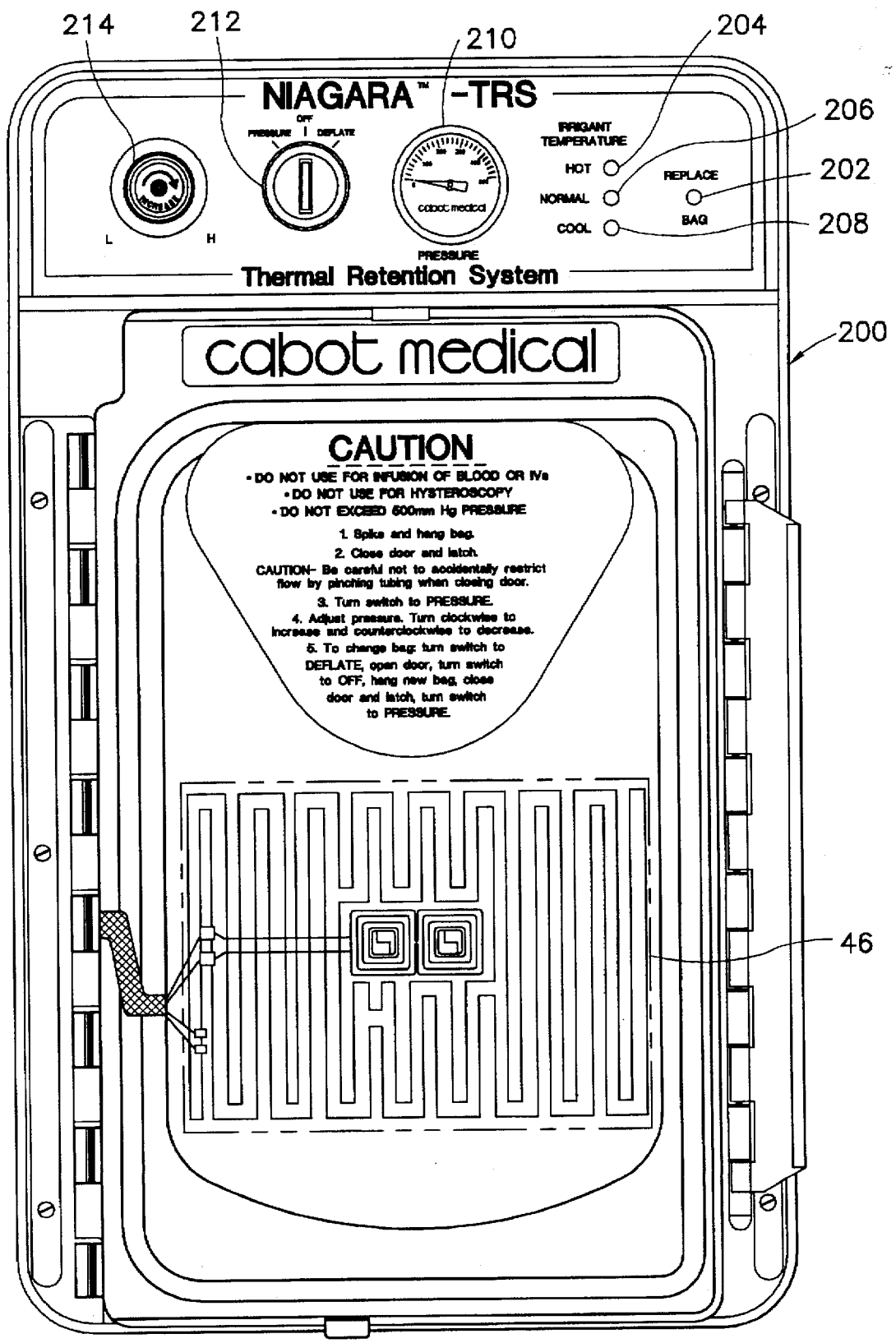
FIG. 10 is a front view of another fluid pump embodiment adapted for use in a thermal retention system according to this invention.

FIG. 10 shows another embodiment of a thermal retention system according to this invention. The thermal retention system embodiment shown in FIG. 10 has a pump 200 which operates in the same way as pump 14 of thermal retention system 10. However, pump 200 differs slightly in its display and control. Pump 200 has an LED indicator 202 for indicating when one or more irrigation fluid bags within pump 200 is empty and ready for replacement. Pump 200 also has LED indicators 204, 206 and 208 for indicating hot, normal and cool fluid temperature conditions, respectively, measured by heat sensor 104 in heating element assembly 46. Indicators 204, 206 and 208 are actuated at pre-set temperature limits including a normal temperature range as well as maximum and minimum temperatures. Indicators 204, 206 and 208 are optionally replaced or supplemented with a digital LED or LCD temperature display like digital temperature display 30 shown in FIG. 2.

Like pump 14, pump 200 has a pressure gauge 210 and a regulator knob 214. Unlike pump 14, pump 200 has a dial 212 to control inflation and deflation of bladder 52. Specifically, turning dial 212 to the right places the thermal retention system into a "deflate" mode, turning dial 212 to the left actuates a "pressure" or "inflate" mode and a neutral position maintains pressure equilibrium.

Figure 11:
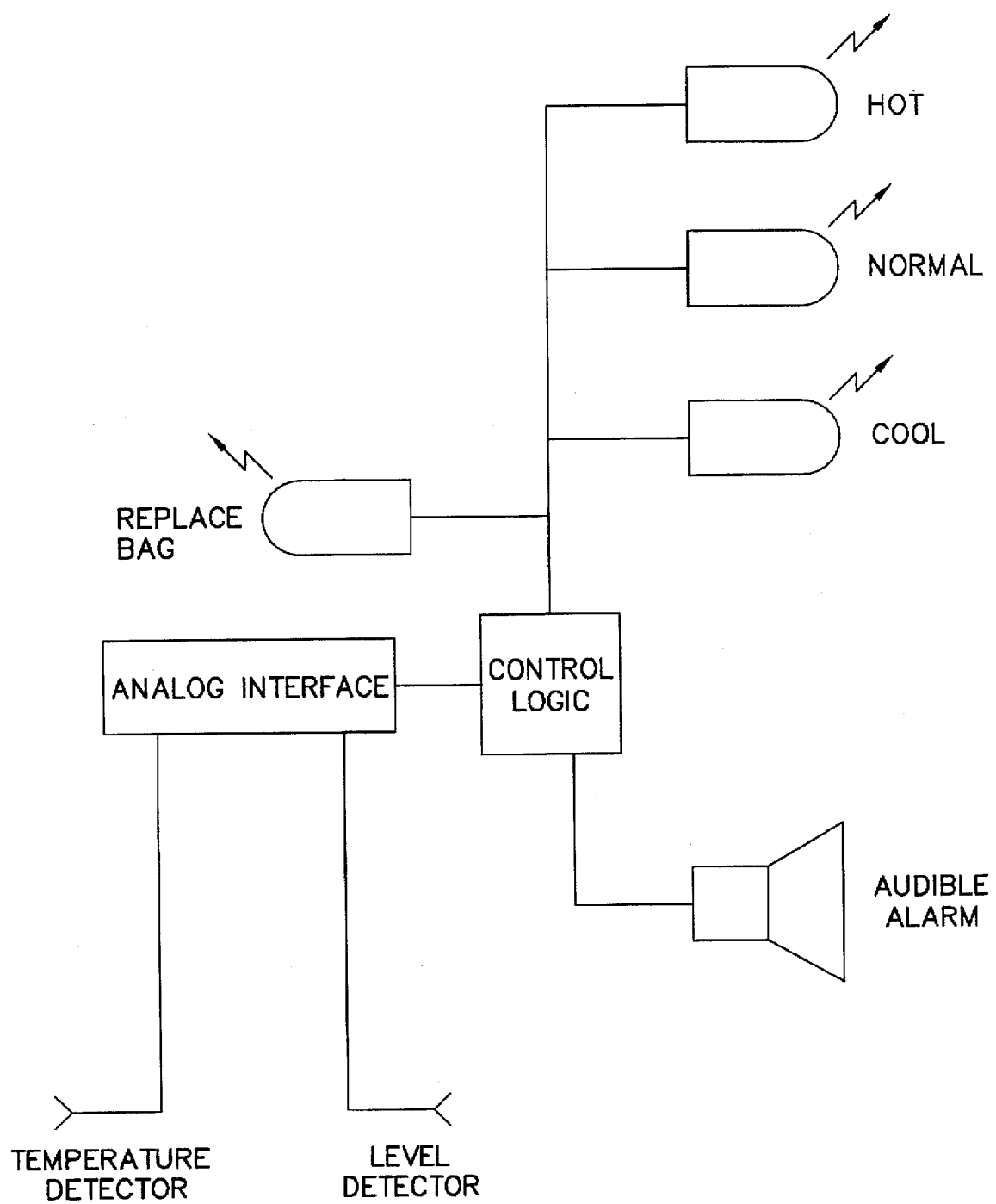
FIG. 11 is a schematic illustrating visual and audio output from the fluid pump embodiment shown in FIG. 10.

Referring to FIG. 11, a schematic shows the preferred logic used in pump 200. As shown in FIG. 11, the system interfaces input from a fluid level detector and a fluid temperature detector. The fluid temperature detector is heat sensor 104 (FIG. 8) and the fluid level detector is any known level detection device. Based on those inputs, control logic activates one of several possible responses. Specifically, a signal from the level detector indicating a low fluid level will activate a visual indicator, such as indicator 202 (FIG. 10), to replace the fluid bag or bags.

Depending upon the input from the temperature detector, the cold, normal or hot indicator will be activated. In other words, when the temperature detected is within a pre-set normal or optimal range, a NORMAL indicator, such as indicator 206 in FIG. 10, will be activated. The normal range is preferably between about 35° C. and 41° C. When the temperature exceeds this normal range, a HOT indicator, such as indicator 204 in FIG. 10, will be activated. Finally, when the temperature is below the optimal temperature range, the COOL indicator, such as indicator 208 in FIG. 10, is activated. When the fluid temperature exceeds a predetermined maximum temperature (preferably 45° C.), the control logic interrupts the power supply to heating element 100 and causes activation of an audible alarm to assure that the operator learns of this condition. Most preferably, a visual alarm is activated if temperature exceeds 42°±1° C. and an audible alarm is activated if temperature exceeds 45°±1° C. The indicators are optionally visual, audible or a message is optionally provided in any other known manner.

Operation of thermal retention system 10 will now be described with reference to the figures.

One or more full irrigation fluid bags are optionally pre-warmed to a temperature approximating that of the surgical patient. Specifically, for human patients, irrigation fluid bags are optionally pre-warmed to a temperature in the range of about 35° to about 45° C. It is also contemplated that irrigation fluid bags are not pre-warmed and are provided at or even below room temperature.

Pump door 34 on pump housing 18 is opened by an operator to provide access to the space between the inside surface of outwardly-curved window 44 on door 34 and flat surface 92 of bladder 52. The operator then places one or more irrigation fluid bags, each on a hook 42 at the top of pump door 34, so that the bags hang within pump housing 18 in the space between window 44 and bladder 52. Each bag is "spiked" for connection to fluid delivery tubing 16.

The operator then closes pump door 34 and locks door 34 in a closed position by pivoting clasp 38 over the outer edge of door 34. The operator connects gas supply line 45 of pump housing 18 to a source of gas pressure. The gas may be air, carbon dioxide, or any other suitable or available gas supply. The pressurized gas supply is preferably regulated between about 45 and 55 PSI.

The operator activates the pump by pushing button 26 shown in FIG. 2 or turning dial 212 to PRESSURE as shown in FIG. 10. Referring to FIG. 6, pushing button 26 causes pressurized gas to flow through pressure regulator 78 and relief valve 80 and into bladder 52. Dial 212 in FIG. 10 is connected to a three-way valve. When dial 212 is set to OFF, the system is in an off state. When dial 212 is set to PRESSURE, bladder 52 is inflated, pressurizing the fluid bag to the selected pressure. The operator may then adjust regulator knob 28 to obtain a desired pressure and monitor the pressure in bladder 52 via pressure gauge 22.

As bladder 52 inflates, flat surface 92 of bladder 52 is pressed against the irrigation fluid bag or bags and forces each bag against window 44 in door 34. As the pressure in bladder 52 is increased, the force also increases, thereby increasing fluid flow from the fluid bag or bags.

During the surgical procedure, the operator visually monitors the level of irrigation fluid in the fluid bag through window 44 in door 34. In the embodiment shown in FIG. 10, indicator 202 would be activated when fluid level falls below a predetermined value. When the fluid bag is empty or nearly empty, the operator deflates bladder 52 using toggle switch 24 (FIG. 6) or dial 212 (FIG. 10). Referring to FIG. 6, switching toggle switch 24 to the left causes actuator 88 to discharge pressurized gas to vacuum ejector 90, thereby deflating bladder 52. Setting dial 212 to DEFLATE also evacuates bladder 52 to vacuum ejector 90. Deflation of bladder 52 releases the force of flat surface 92 against the fluid bag or bags and decreases fluid pressure and flow rate.

Figure 8:
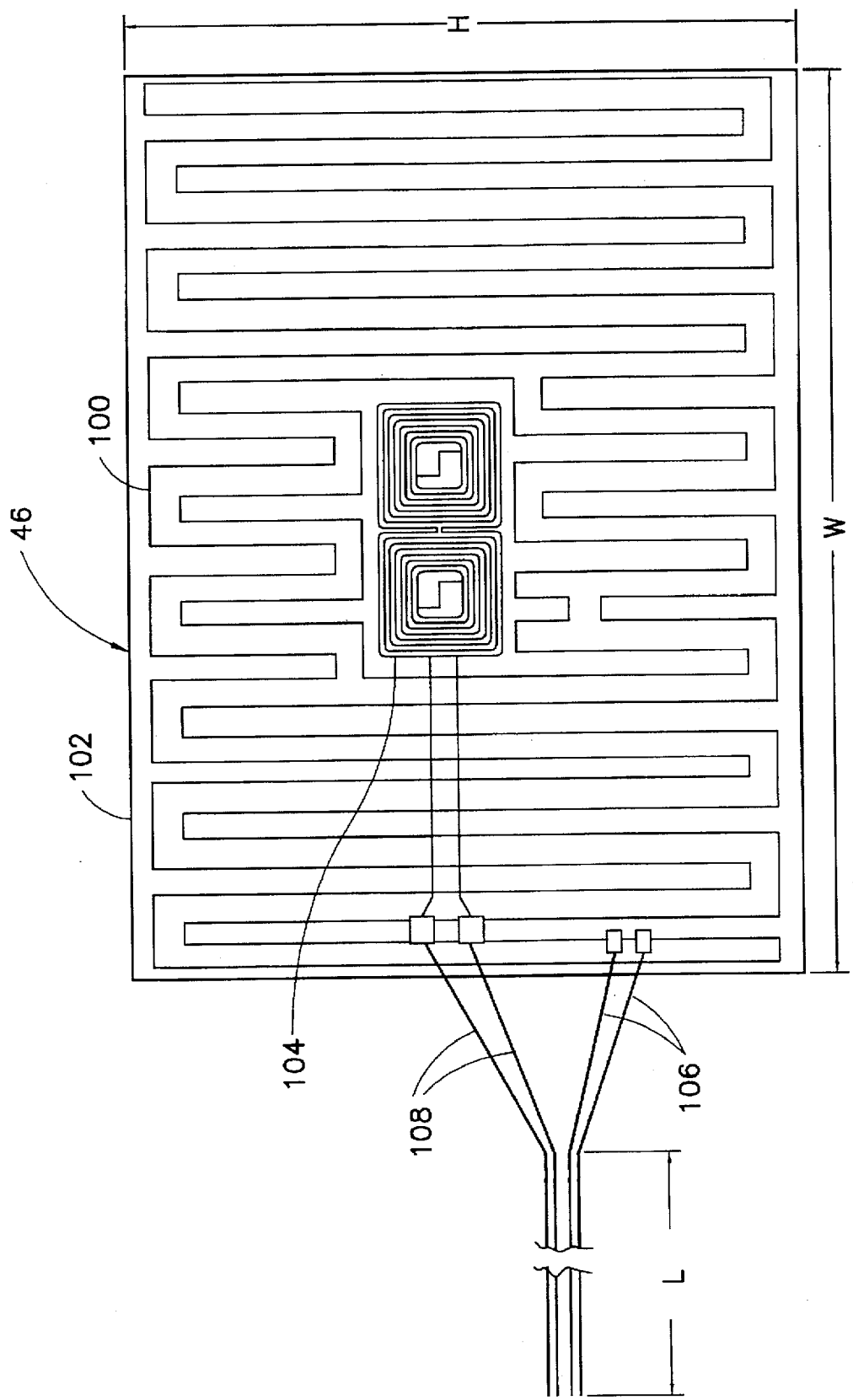
FIG. 8 is a front view of one form of heating element assembly adapted for use in a thermal retention system embodying features of this invention.

Referring now to FIG. 8, power supplied to heating element 100 of heating element assembly 46 through conductors 106 generates heat due to resistance in heating element 100. This heat causes radiant heat transfer to fluid in each irrigation fluid bag. Also, contact between window 44 and each fluid bag causes conductive heat transfer from heating element 100 to the fluid. The power supply is preferably low wattage to prevent rapid thermal runaway.

Heat transfer from heating element 100 maintains the elevated temperature of pre-warmed irrigation fluid or heats and maintains an elevated temperature in irrigation fluid that has not been pre-warmed.

Heat sensor 104 monitors the fluid temperature, sending a signal to heater control unit 20 via conductors 108. Heating element 100 is controlled by heater control unit 20 to maintain an optimum temperature approximating the patient's body temperature throughout the surgical procedure. Heater control unit 20 preferably maintains fluid temperature at about 38° C.

A study of the rate of cooling of pre-warmed bags of water was performed. The results are presented in the following examples.

EXAMPLE

Figure 12:
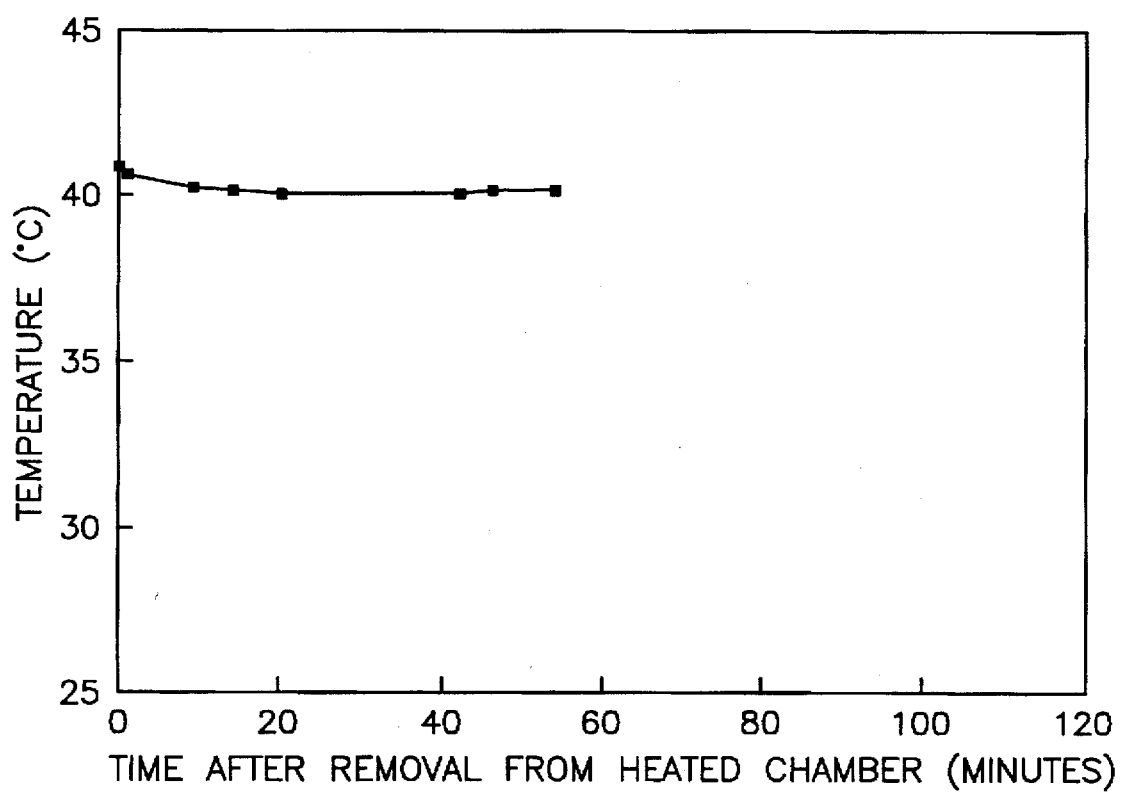
FIG. 12 is a graph illustrating the relationship between temperature and time for water retained within a thermal retention system according to this invention.

A three-liter bag of water was pre-warmed in a heated chamber for 14 hours to a temperature of 41° C. The pre-warmed bag was removed from the heated chamber and placed into an irrigation pump housing according to this invention. The temperature of the water was measured over time with the heating element assembly of the pump fully operational. FIG. 12 is a graph illustrating the relationship between water temperature in degrees Centigrade and elapsed time in minutes. As shown in the graph, the temperature of the water remained substantially constant for the duration of the study (more than 55 minutes).

COMPARATIVE EXAMPLE

Figure 13:
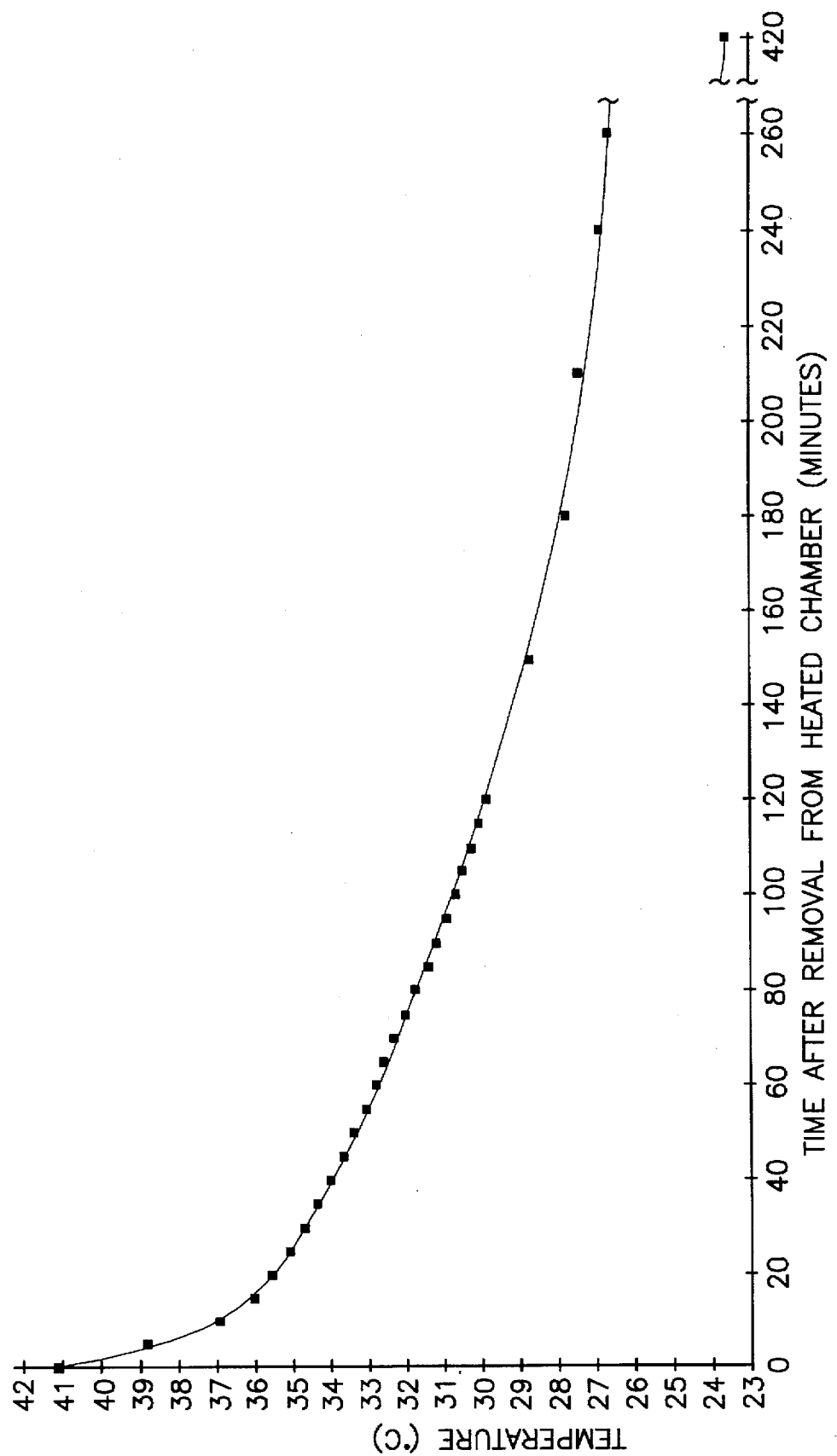
FIG. 13 is a graph illustrating the relationship between temperature and time for water retained in a pump which does not conform to aspects of this invention.

A three-liter bag of water was pre-warmed in a heated chamber for 14 hours to a temperature of 41° C. as in the preceding Example. The pre-warmed bag was removed from the heated chamber and placed into an irrigation pump housing according to this invention. The water temperature was measured over time, this time without use of the heating element assembly. The results are shown in FIG. 13, which is a graph illustrating the relationship between temperature in degrees Centigrade and elapsed time in minutes. As can be seen in FIG. 13, with no external heat source the temperature of the three-liter water bag dropped over 8° C. in the first hour. The water cooled to almost 23° C. over the duration of the test, which lasted about 420 minutes.

Accordingly a thermal retention system according to this invention is capable of maintaining a substantially constant fluid temperature throughout an operative procedure. Without a thermal retention system according to this invention, fluid remains cool at or around room temperature. Also, pre-warmed fluid rapidly cools to a temperature well below the patient's body temperature.

Many modifications can be made to the thermal retention system embodiments shown in the drawings without going beyond the scope or spirit of this invention. The scope of the invention is described separately in the claims that follow.

For example, the power provided to heating element 100 is optionally alternated to provide heating element 100 with a dual function. Specifically, when the power is off, heating element 100 can be used as a secondary RTD-type sensor.

Heating element 100 so used provides a back-up to heat sensor 104. When the power is on, heating element 100 provides a radiant and conductive heat source. Accordingly, a safety system is available if power to heating element 100 is pulsed and heating element 100 is used alternately as a heat source and heat sensor.

The thermal retention system embodiment shown in FIG. 10 can be modified by replacing temperature indicators 204, 206 and 208 with a digital temperature display. Such a display may be in the form of a digital LED or LCD display or can optionally be in the form of an analog display.

It is contemplated that the thermal retention system of this invention can utilize any fluid delivery system other than the bladder-driven system shown in the figures. For example, the thermal retention system optionally utilizes gravity-feed, syringe/piston or any other known mechanical, pneumatic or hydraulic fluid delivery system.

Although the heater of the thermal retention system is preferably located on the window of a pump housing door, the heater is optionally located anywhere in the system so long as sufficient heat transfer is maintained between the heater and the irrigation fluid. For example, the heater may be positioned on a housing wall or on a windowless housing door. It is contemplated that a heater is optionally formed integral with the bladder of a bladder-driven delivery system. The heater is optionally made a part of disposable irrigation fluid bags for connection to a thermal retention system according to this invention.

The thermal retention system of this invention is preferably used for irrigation fluids during surgical procedures. It is also contemplated that the system optionally heats and maintains the temperature of any fluid, liquid or gaseous, for any medical or non-medical application.

In any embodiment, this invention provides a safe, reliable and efficient system and method for heating and maintaining irrigation fluid at or near a patient's body temperature throughout a surgical procedure.

What is claimed is:

1. An apparatus for heating a fluid to be introduced into a patient from at least one bag during a medical procedure so that the body temperature of said patient does not fall below a safe body temperature, and for delivering said fluid from said at least one bag to said patient, said apparatus comprising:

a housing sized and shaped to enclose said at least one bag containing said fluid, said housing including a door positioned to provide access to an interior of said housing when said door is in an open position;

pump means mounted in said interior of said housing and positioned within said interior of said housing for exerting a force against said at least one bag containing said fluid;

a heater attached to said door of said housing for transferring heat to said fluid in said at least one bag within said housing when said door of said housing is in a closed position; and a temperature sensor attached to said door of said housing and positioned for sensing a temperature of said fluid in said at least one bag when said door is in said closed position.

2. The apparatus described in claim 1, wherein said pump means is an inflatable bladder connected to a source of pressurized fluid for inflation of said inflatable bladder to exert said force against said at least one bag containing said fluid, said inflatable bladder also being connected to an outlet for said pressurized fluid for deflation of said inflatable bladder to reduce said force against said at least one bag.

3. The apparatus described in claim 1, wherein said fluid is irrigation fluid.

4. The apparatus described in claim 1, wherein said fluid is pre-warmed.

5. The apparatus described in claim 4, wherein said pre-warmed fluid has a temperature in the range of from about 35° to about 45° C.

6. The apparatus described in claim 1, wherein said temperature sensor is a resistance temperature device.

7. The apparatus described in claim 1, further comprising means connected to said heater and to said temperature sensor for controlling the temperature of said fluid in said at least one bag.

8. The apparatus described in claim 7, wherein said means for controlling is calibrated to control said heater to maintain said temperature of said fluid at a temperature within the range of from about 35° C. to about 45° C.

9. The apparatus described in claim 8, wherein said means for controlling is calibrated to control said heater to maintain said temperature of said fluid at a temperature of about 38° C.

10. The apparatus described in claim 8, further comprising means for indicating when said temperature of said fluid falls below about 35° C., is in the range of from about 35° C. to about 41° C., and exceeds about 41° C.

11. The apparatus described in claim 8, further comprising means for providing an audible alarm when said temperature of said fluid exceeds about 45° C.

12. The apparatus described in claim 1, further comprising means connected to said temperature sensor for displaying said temperature of said fluid.

13. An apparatus for heating at least one bag containing a fluid to be introduced into a patient during a medical procedure so that a body temperature of said patient does not fall below a safe body temperature, and for pumping said fluid from said at least one bag to said patient, said apparatus comprising:

housing means having an interior region sized and shaped to accommodate said at least one bag containing said fluid, said housing means having an opening for insertion and removal of said at least one bag containing said fluid and a door positioned for covering said opening in said housing means;

pump means mounted within said housing means and positioned adjacent said interior region of said housing means, said pump means being actuable for exerting force against said at least one bag in said interior region;

heating means attached to said door of said housing means and positioned for transferring heat to said fluid in said at least one bag;

temperature sensing means attached to said door of said housing means for sensing a temperature of said fluid in said at least one bag; and controller means connected to said heating means and said temperature sensing means for controlling said heating means and for maintaining said temperature of said fluid in said at least one bag within a predetermined temperature range.

14. The apparatus described in claim 13, wherein said fluid is irrigation fluid.

15. The apparatus described in claim 13, wherein said fluid is pre-warmed.

16. The apparatus described in claim 15, wherein said pre-warmed fluid has a temperature within the range of from about 35° to about 45° C.

17. The apparatus described in claim 13, wherein said predetermined temperature range is from about 35° C. to about 45° C.

18. The apparatus described in claim 17, wherein said controller means is calibrated for heating and maintaining said temperature of said fluid in said at least one bag at a target temperature of about 38° C.

19. The apparatus described in claim 13, wherein said pump means is an inflatable bladder having an inflated position for exerting said force against said at least one bag and having a deflated condition for reducing said force.

20. The apparatus described in claim 13, wherein said temperature sensing means is a resistance temperature device attached to said door of said housing means.

21. A method for maintaining the temperature of fluid to be introduced into a patient from at least one bag so that a body temperature of said patient does not fall below a safe body temperature, and for delivering said fluid from said at least one bag and to said patient, said method comprising the steps of:

providing a housing sized and shaped to accommodate said at least one bag containing said fluid, a door mounted on said housing, and pump means mounted within said housing;

placing said at least one bag containing said fluid in said interior of said housing between said door and said pump means;

providing a heat source attached to said door of said housing for transferring heat to said fluid in said at least one bag when said door is in a closed position;

providing a temperature sensor attached to said door for sensing the temperature of said fluid;

controlling said heat source to maintain the temperature of said fluid in said at least one bag so that it approximates said body temperature of said patient; and activating said pump means to exert a force against said at least one bag and cause delivery of said fluid from said at least one bag and to said patient.

22. The method described in claim 21, further comprising the step of pre-warming said fluid in said at least one bag to a temperature approximating said body temperature of said patient.

23. The method described in claim 22, wherein said step of pre-warming said fluid in said at least one bag includes warming said fluid to a temperature in the range of from about 35° C. to about 45° C.

24. The method described in claim 21, wherein said step of controlling said heat source includes maintaining said temperature of said fluid within a range of from about 35° C. to about 45° C.

25. The method described in claim 24, wherein said step of controlling said heat source includes maintaining a target temperature of about 38° C.

26. The method described in claim 21, wherein said step of actuating said pump means includes inflating an inflatable bladder so that said inflatable bladder contacts said at least one bag containing said fluid.

27. The method described in claim 21, further comprising the steps of spiking said at least one bag of said fluid and connecting said at least one bag to a delivery tube.

28. An apparatus for heating a fluid to be introduced into a patient from at least one bag during a medical procedure so that a body temperature of a patient does not fall below a safe body temperature, and for delivering said fluid from said at least one bag to a patient, said apparatus comprising:

a housing sized and shaped to enclose said at least one bag containing said fluid, said housing including a door positioned to provide access to an interior of said housing when said door is in an open position;

pump means mounted in said interior of said housing and positioned within said interior of said housing for exerting a force against said at least one bag containing said fluid;

a heater mounted adjacent said door of said housing for transferring heat to said fluid in said at least one bag within said housing when said door of said housing is in a closed position, said heater including an electrical resistance wire connected to a power source; and means for alternating power delivered from said power source to said electrical resistance wire between power on and power off conditions, wherein said electrical resistance wire is alternatively used as a resistance temperature device when said power is off or as said heater when said power is on.

29. An apparatus for heating at least one bag containing a fluid to be introduced into a patient during a medical procedure so that a body temperature of a patient does not fall below a safe body temperature, and for pumping said fluid from said at least one bag to a patient, said apparatus comprising:

housing means having an interior region sized and shaped to accommodate said at least one bag containing said fluid, said housing means having an opening for insertion and removal of said at least one bag containing said fluid and a door positioned for covering said opening in said housing means;

pump means mounted within said housing means and positioned adjacent said interior region of said housing means, said pump means being actuable for exerting force against said at least one bag in said interior region;

heating means mounted adjacent said door of said housing means and positioned for transferring heat to said fluid in said at least one bag, said heating means including an electrical resistance wire attached to said door of said housing means and connected to a power source;

means for alternating power delivered from said power source to said electrical resistance wire between power on and power off conditions, wherein said electrical resistance wire is alternately used as a resistance temperature device when said power is off and as said heating means when said power is on; and controller means connected to said heating means and said temperature sensing means for controlling said heating means and for maintaining said temperature of said fluid in said at least one bag within a predetermined temperature range.

* * * * *